(12) United States Patent
Ho

(10) Patent No.: US 10,101,291 B2
(45) Date of Patent: Oct. 16, 2018

(54) MOBILE DEVICE HAVING GAS-SENSING FUNCTION

(71) Applicant: Winbond Electronics Corp., Taichung (TW)

(72) Inventor: Yu-Hsuan Ho, Taichung (TW)

(73) Assignee: Winbond Electronics Corp., Taichung (TW)

( * ) Notice: Subject to any disclaimer, the term of this patent is extended or adjusted under 35 U.S.C. 154(b) by 211 days.

(21) Appl. No.: 15/364,177

(22) Filed: Nov. 29, 2016

(65) Prior Publication Data

US 2017/0261454 A1    Sep. 14, 2017

(30) Foreign Application Priority Data

Mar. 11, 2016  (CN) .......................... 2016 1 0139127

(51) Int. Cl.
| | |
|---|---|
| *G01N 27/00* | (2006.01) |
| *G01N 27/12* | (2006.01) |
| *G01N 33/00* | (2006.01) |
| *H04M 1/725* | (2006.01) |
| *H04M 1/02* | (2006.01) |
| *H04M 1/21* | (2006.01) |

(52) U.S. Cl.
CPC ....... *G01N 27/125* (2013.01); *G01N 33/0036* (2013.01); *H04M 1/725* (2013.01); *G01N 27/127* (2013.01); *H04M 1/026* (2013.01); *H04M 1/21* (2013.01); *H04M 2250/12* (2013.01)

(58) Field of Classification Search
CPC .... G01N 27/125; G01N 27/04; G01N 27/127; G01N 33/0036; G01N 33/0009; H04M 1/725; H04M 1/21; H04M 1/026; H04M 2250/12
See application file for complete search history.

(56) References Cited

U.S. PATENT DOCUMENTS

| | | |
|---|---|---|
| 4,708,941 A | 11/1987 | Giuliani |
| 5,841,021 A | 11/1998 | De Castro et al. |
| 8,785,924 B2 | 7/2014 | Jang et al. |

(Continued)

FOREIGN PATENT DOCUMENTS

| | | |
|---|---|---|
| CN | 1741652 | 3/2006 |
| CN | 104937385 | 9/2015 |

(Continued)

OTHER PUBLICATIONS

Cheng-Xian Lin, "A visible light activated tungsten trioxide based sensor for gas sensing at room temperature," master's thesis, Institute of Optoelectronic Sciences, National Taiwan Ocean University, Jul. 2011.

(Continued)

*Primary Examiner* — Blake A Tankersley
(74) *Attorney, Agent, or Firm* — JCIPRNET

(57) ABSTRACT

A mobile device having a gas-sensing function including a case body, a backlight module and a gas sensor is provided. The case body has at least one through hole. The backlight module is disposed in the case body. The gas sensor is disposed in the case body. The gas sensor includes a gas-sensing material layer for sensing a gas. The gas-sensing material layer receives a visible light emitted from the backlight module and is activated by the visible light.

12 Claims, 3 Drawing Sheets

(56) References Cited

U.S. PATENT DOCUMENTS

| | | | | |
|---|---|---|---|---|
| 2006/0000259 A1* | 1/2006 | Rothschild | ............ | G01N 27/125 |
| | | | | 73/31.06 |
| 2010/0077840 A1* | 4/2010 | Srivastava | ............ | G01N 27/305 |
| | | | | 73/31.05 |
| 2014/0134053 A1* | 5/2014 | Mayer | ................ | G01N 33/0009 |
| | | | | 422/83 |
| 2015/0212549 A1 | 7/2015 | Shin et al. | | |
| 2017/0254779 A1* | 9/2017 | Wang | .................... | G01N 27/125 |

FOREIGN PATENT DOCUMENTS

| | | |
|---|---|---|
| CN | 104958073 | 10/2015 |
| TW | 201445126 | 12/2014 |
| WO | 2015045411 | 4/2015 |
| WO | 2015126306 | 8/2015 |

OTHER PUBLICATIONS

"Office Action of Taiwan Counterpart Application", dated Oct. 12, 2016, p. 1-p. 5.

* cited by examiner

MOBILE DEVICE HAVING GAS-SENSING FUNCTION

CROSS-REFERENCE TO RELATED APPLICATION

This application claims the priority benefit of China application serial no. 201610139127.0, filed on Mar. 11, 2016. The entirety of the above-mentioned patent application is hereby incorporated by reference herein and made a part of this specification.

BACKGROUND OF THE INVENTION

Field of the Invention

The invention relates to a mobile device, and particularly relates to a mobile device having a gas-sensing function.

Description of Related Art

In recent years, with the progress of industrial civilization, people have paid more attention to their own health and environmental protection, and the demands for related industries have grown explosively. Gas-sensing technology for use in the monitoring of the gas exhaled by human (e.g., biological markers for human diseases, alcohol concentration) or the environmental pollution gas has the development prospect.

In order to achieve the purpose of portable gas sensing, a gas sensor which can be integrated in a mobile device is more important. Additionally, in order to achieve the purpose of portable use, the prerequisite is that the gas sensor must be able to work at room temperature. Therefore, how to enable the gas sensor to sense the gas at room temperature is also a target for research and development in the industry currently.

SUMMARY OF THE INVENTION

The invention provides a mobile device having a gas-sensing function, which can achieve the purpose of portable gas sensing and can sense the gas at room temperature.

The invention provides a mobile device having a gas-sensing function including a case body, a backlight module and a gas sensor. The case body has at least one through hole. The backlight module is disposed in the case body. The gas sensor is disposed in the case body. The gas sensor includes a gas-sensing material layer for sensing a gas. The gas-sensing material layer receives a visible light emitted from the backlight module and is activated by the visible light. An existence of the gas is determined by measuring a change of a resistance value of the activated gas-sensing material According to an embodiment of the invention, in the mobile device having the gas-sensing function, the through hole is a through hole of a loudspeaker, a through hole of a microphone, or an air guide through hole of the mobile device, for example.

According to an embodiment of the invention, in the mobile device having the gas-sensing function, the backlight module may have a light guide plate. The light guide plate includes a light emitting surface, a light incident surface, a sub-light emitting surface, and a bottom surface. The light emitting surface is disposed opposite to the bottom surface, and the light incident surface is disposed opposite to the sub-light emitting surface. The gas sensor may be coupled to the sub-light emitting surface of the light guide plate or disposed at a back surface of the backlight module.

According to an embodiment of the invention, in the mobile device having the gas-sensing function, an energy gap of the gas-sensing material layer is 1.24 eV to 12.4 eV, for example.

According to an embodiment of the invention, in the mobile device having the gas-sensing function, a material of the gas-sensing material layer is metal oxide or grapheme oxide, for example.

According to an embodiment of the invention, in the mobile device having the gas-sensing function, the metal oxide is tungsten oxide ($WO_3$) or iron oxide ($Fe_2O_3$), for example.

According to an embodiment of the invention, in the mobile device having the gas-sensing function, a method of foil ling the gas-sensing material layer is a three dimensional printing method, an inkjet printing method, a gravure printing method, a screen printing method, a flexo printing method, or an offset printing method, for example.

According to an embodiment of the invention, in the mobile device having the gas-sensing function, a gas sensed by the gas sensor is a volatile organic compound (VOCs) or carbon dioxide, for example.

According to an embodiment of the invention, in the mobile device having the gas-sensing function, the gas sensor further includes a first electrode and a second electrode. The first electrode and the second electrode are separate from each other and connected to the gas-sensing material layer.

According to an embodiment of the invention, in the mobile device having the gas-sensing function, the gas sensor further includes a filter membrane. The filter membrane covers the gas-sensing material layer.

According to an embodiment of the invention, in the mobile device having the gas-sensing function, a material of the filter membrane is a nanoporous material, for example. The nanoporous material is a polymer or anodic aluminum oxide, for example.

According to an embodiment of the invention, in the mobile device having the gas-sensing function, the mobile device includes a mobile phone, a tablet computer, a notebook computer, a portable game machine, or a portable music player device.

Based on the above, in the mobile device having the gas-sensing function provided by the invention, since the gas sensor is integrated into the mobile device, and the gas-sensing material layer can be activated by the visible light emitted from the backlight module to sense the gas, the mobile device can achieve the purpose of the portable gas sensing and can sense the gas at room temperature.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
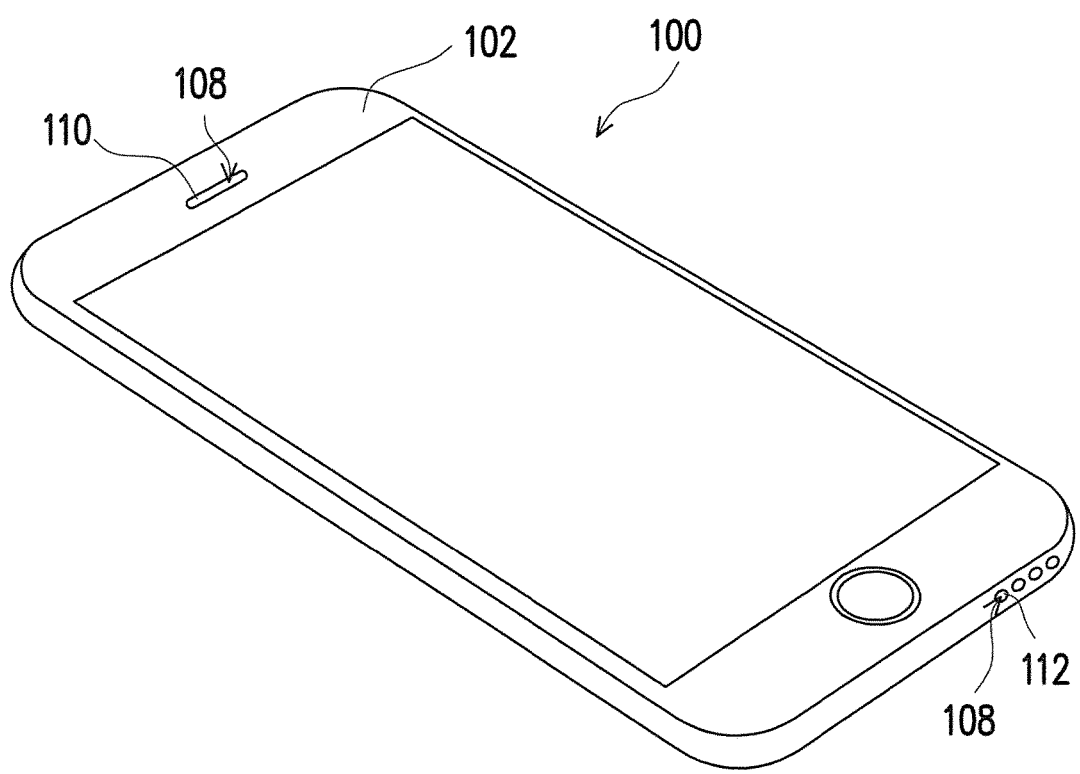
FIG. 1 is a schematic view of a mobile device having a gas-sensing function of an embodiment of the invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
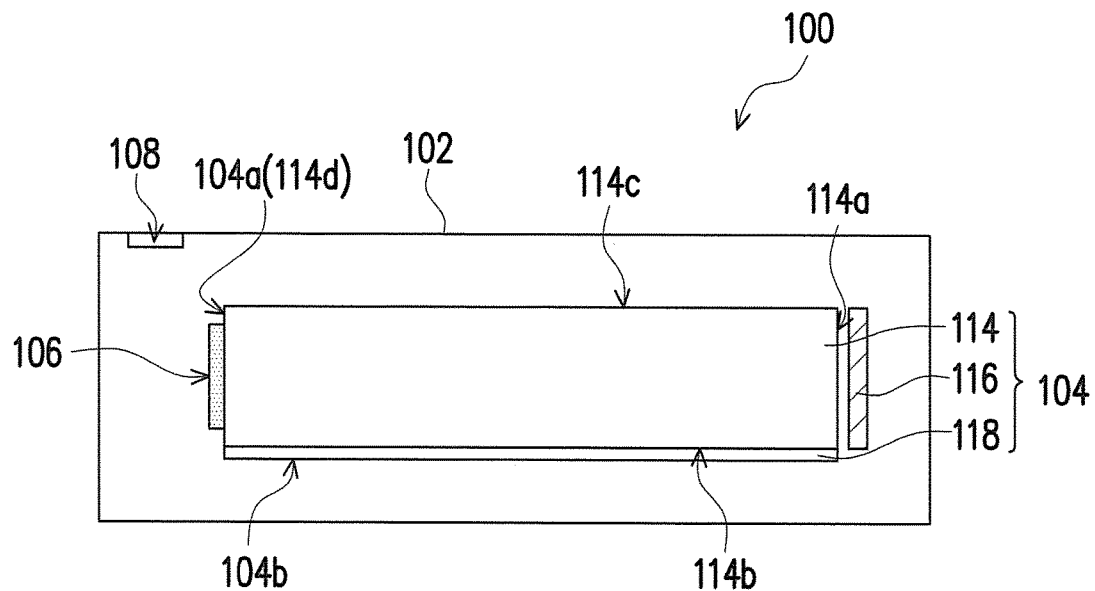
FIG. 2 is a schematic cross-sectional view of a configuration relationship between a through hole of a loudspeaker, a backlight module, and a gas sensor of FIG. 1.
Figure 3:
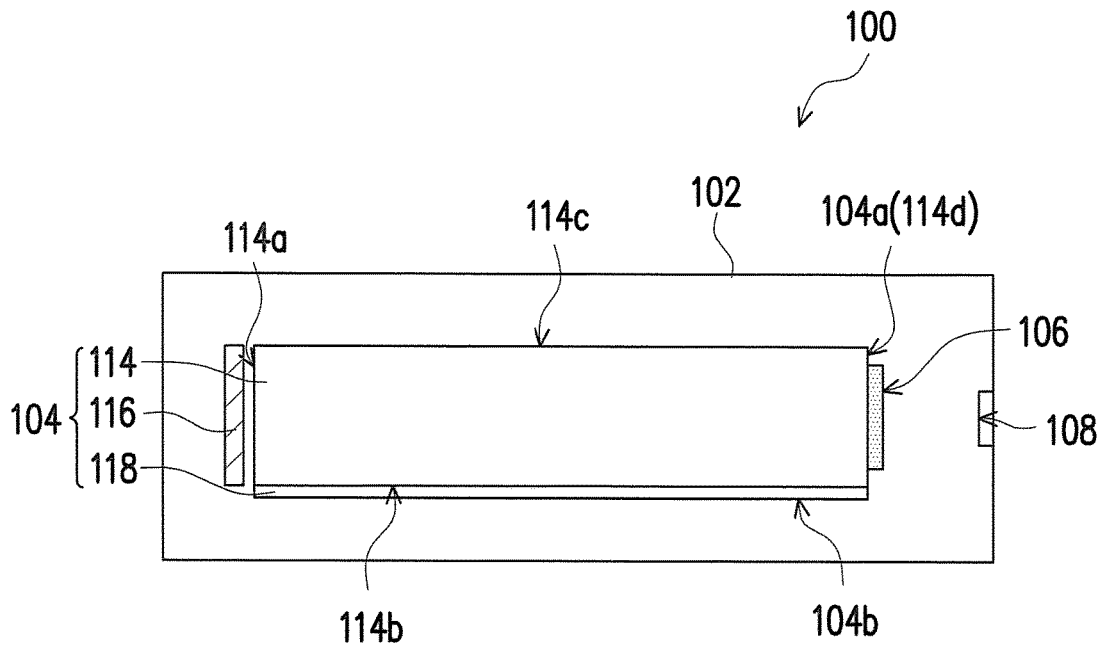
FIG. 3 is a schematic cross-sectional view of a configuration relationship between a through hole of a microphone, a backlight module, and a gas sensor of FIG. 1.
Figure 4:
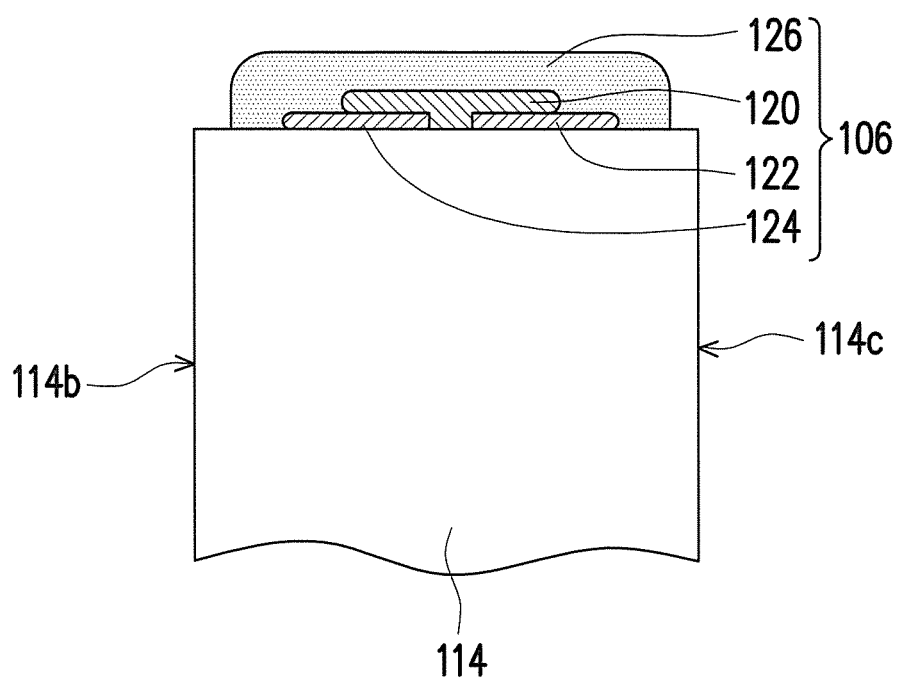
FIG. 4 is an enlarged view of the gas sensor and the light guide plate in FIG. 2 and FIG. 3.

FIG. 1 is a schematic view of a mobile device having a gas-sensing function of an embodiment of the invention. FIG. 2 is a schematic cross-sectional view of a configuration relationship between a through hole of a loudspeaker, a backlight module, and a gas sensor of FIG. 1. FIG. 3 is a schematic cross-sectional view of a configuration relationship between a through hole of a microphone, a backlight module, and a gas sensor of FIG. 1. FIG. 4 is an enlarged view of the gas sensor and the light guide plate in FIG. 2 and FIG. 3.

Referring to FIG. 1 to FIG. 3, a mobile device 100 having a gas-sensing function including a case body 102, a backlight module 104, and a gas sensor 106 is provided. The mobile device 100 is a portable electronic device having a screen such as a smart watch, a mobile phone, a tablet computer, a notebook computer, a portable game machine, or a portable music player device. In the present embodiment, the mobile device 100 is the smart phone as an example to illustrate. Additionally, a person skilled in the art may understand that the mobile device 100 further includes other components (e.g., display panels, processors, or communication modules) which are not discussed in the invention, and the description thereof is omitted.

The case body 102 has at least one through hole 108. A material of the case body 102 is glass, metal, or plastic, for example. The through hole 108 may be formed on the case body 102 by a micro drilling method, for example. The through hole 108 is the through hole 108 of a loudspeaker 110, the through hole 108 of a microphone 112, or an air guide through hole (not shown) of the mobile device 100 set additionally.

Referring to FIG. 2 and FIG. 3, the backlight module 104 is disposed in the case body 102. In the present embodiment, the backlight module 104 is a side type backlight module as an example to illustrate. However, the invention is not limited thereto. The backlight module 104 includes a light guide plate 114, a visible light source 116, and a reflection sheet 118. The light guide plate 114 includes a light incident surface 114a, a bottom surface 114b, a light emitting surface 114c, and a sub-light emitting surface 114d. In the present embodiment, the bottom surface 114b is disposed opposite to the light emitting surface 114c, the light incident surface 114a is connected to the bottom surface 114b and the light emitting surface 114c, and the sub-light emitting surface 114d is disposed opposite to the light incident surface 114a. The light incident surface 114a and the sub-light emitting surface 114d are disposed near a side surface 104a of the backlight module 104. The bottom surface 114b is disposed near a back surface 104b of the backlight module 104. The visible light source 116 is coupled to the light incident surface 114a of the light guide plate 114 and emits light toward the light incident surface 114a. After the light enters the light guide plate 114 through the light incident surface 114a, most of the light emits from the light emitting surface 114c, and part of the light emits from the sub-light emitting surface 114d. The visible light source 116 is a light emitting diode (LED) or an organic light emitting diode (OLED), for example. The reflection sheet 118 may be disposed on the bottom surface 114b of the light guide plate 114 to reflect the light emitted from the bottom surface 114b of the light guide plate 114 back to the light guide plate 114. The bottom surface 114b of the light guide plate 114 can form a plurality of dots (not shown) to destroy the total reflection, so that the light is emitted from the light emitting surface 114c of the light guide plate 114.

Referring to FIG. 1 to FIG. 3, the gas sensor 106 is disposed in the case body 102. The mobile device 100 may have at least one gas sensor 106, and the gas sensor 106 may be disposed near the through hole 108 of the loudspeaker 110, the through hole 108 of the microphone 112, or the air guide through hole (not shown) set additionally. As long as the setting method of the gas sensor 106 that the gas sensor 106 is able to sense the gas to be sensed entering into the case body 102 through the through hole 108, it belongs to the scope of the invention.

The gas sensor 106 may be coupled to the sub-light emitting surface 114d of the light guide plate 114 to receive the light of the visible light source 116 transmitted by the light guide plate 114, so as to avoid affecting the image quality of the front surface of the screen. However, the setting method of the gas sensor 106 is not limited thereto. As long as the setting method of the gasسensor 106 that the gas sensor 106 is able to receive the visible light emitted from the backlight module 104, it belongs to the scope of the invention. In the present embodiment, the gas sensor 106 is disposed at the sub-light emitting surface 114d as an example to illustrate. In another embodiment, the gas sensor 106 may be disposed at the bottom surface 114b of the light guide plate 114, or the back surface 104b of the backlight module 104. In the case that the gas sensor 106 is disposed at the back surface 104b of the backlight module 104, light guide devices (e.g., optical fibers) set additionally are required to guide the light to the gas sensor 106.

A variety of gas sensings can be performed by the gas sensor 106. The gas sensed by the gas sensor 106 is a volatile organic compound (VOCs) or carbon dioxide, for example. The volatile organic compounds are alkyl compounds, alkenyl compounds, phenyl compounds, alcohol compounds, aldehyde compounds, ketone compounds, nitrogen-containing organic compounds, or alkyl halide compounds, for example. The alkyl compound is methane, ethane, propane, or butane, for example. The alkenyl compound is ethylene, propylene, or butene, for example. The phenyl compound is benzene, toluene, ethylbenzene, or xylene, for example. The alcohol compound is methanol, ethanol (alcohol), isopropyl alcohol, or isoamyl alcohol, for example. The aldehyde compound is formaldehyde or acetaldehyde, for example. The ketone compound is acetone or butanone, for example. The nitrogen-containing organic compound is acrylonitrile, for example. The alkyl halide compound is chloromethane, chloroform, carbon tetrachloride, trichloroethylene, or tetrachloroethylene, for example.

Referring to FIG. 4, the gas sensor 106 includes a gas-sensing material layer 120. The gas-sensing material layer 120 may be disposed on the light guide plate 114. An energy gap of the gas-sensing material layer 120 is 1.24 eV to 12.4 eV, for example. Since the lattice defects often exists in the gas-sensing material layer 120, carriers activated by low energy light can enter the conduction band by absorption for multiple times. In the case that the energy gap of the gas-sensing material layer 120 is 1.24 eV to 12.4 eV, an absorption band of the gas-sensing material layer 120 can be greater than an absorption band of the visible light source 116. For example, the absorption band of the gas-sensing material layer 120 may be between 100 nm and 1000 nm. That is, the gas-sensing material layer 120 can be activated by the visible light. A material of the gas-sensing material layer 120 is metal oxide or grapheme oxide, for example. The metal oxide is tungsten oxide ($WO_3$) or iron oxide ($Fe_2O_3$), for example. A method of forming the gas-sensing material layer 120 is, for example, a printing method, such as a three dimensional printing method, an inkjet printing method, a gravure printing method, a screen printing method, a flexo printing method, or an offset printing method.

The gas-sensing material layer 120 receives the visible light emitted from the backlight module 104 and is activated by the visible light. Thereby, the gas sensor 106 is able to sense the gas at room temperature. Specifically, after the gas-sensing material layer 120 activated by the visible light is in contact with the gas to be sensed, a resistance value of the gas-sensing material layer 120 will change. Thus, by measuring the change of the resistance value of the gas-sensing material layer 120, whether the gas to be sensed exists or not in the environment can be known.

Additionally, when the concentration of the gas to be sensed is higher, the magnitude of change of the resistance value of the gas-sensing material layer 120 is higher. On the contrary, when the concentration of the gas to be sensed is lower, the magnitude of change of the resistance value of the gas-sensing material layer 120 is lower. Therefore, the concentration of the gas to be sensed can be obtained from the magnitude of change of the resistance value of the gas-sensing material layer 120.

On the other hand, the way of the resistance value change of the gas-sensing material layer 120 is related to the material thereof. For example, the material of the gas-sensing material layer 120 may be an N-type gas-sensing material or a P-type gas-sensing material. When the material of the gas-sensing material layer 120 is the N-type gas-sensing material, the concentration of the gas to be sensed is inversely proportional to the resistance value of the gas-sensing material layer 120. That is, when the concentration of the gas to be sensed is higher, the resistance value of the N-type gas-sensing material layer 120 is lower. On the contrary, when the concentration of the gas to be sensed is lower, the resistance value of the N-type gas-sensing material layer 120 is higher.

When the material of the gas-sensing material layer 120 is the P-type gas-sensing material, the concentration of the gas to be sensed is directly proportional to the resistance value of the gas-sensing material layer 120. That is, when the concentration of the gas to be sensed is higher, the resistance value of the P-type gas-sensing material layer 120 is higher. On the contrary, when the concentration of the gas to be sensed is lower, the resistance value of the P-type gas-sensing material layer 120 is lower.

The gas sensor 106 may further include a first electrode 122 and a second electrode 124. The first electrode 122 and the second electrode 124 are separate from each other and connected to the gas-sensing material layer 120. In the present embodiment, the first electrode 122 and the second electrode 124 are disposed between the gas-sensing material layer 120 and the light guide plate 114 respectively, for example. The first electrode 122 and the second electrode 124 can be used to measure the resistance value of the gas sensor 106. A material of the first electrode 122 and the second electrode 124 is iron, copper, aluminum, magnesium, tin, nickel, gold, silver, lead, or zinc, for example. A method of forming the first electrode 122 and the second electrode 124 is a semiconductor lithography and etching method, a three dimensional printing method, an inkjet printing method, a gravure printing method, a screen printing method, a flexo printing method, or an offset printing method, for example.

Additionally, the gas sensor 106 may further include a filter membrane 126. The filter membrane 126 covers the gas-sensing material layer 120 for screening gas, so that only the specific gas to be sensed can be passed through. For example, when the filter membrane 126 is selected for screening ethanol (alcohol), the mobile device 100 can be used as a portable alcohol testing device. When the filter membrane 126 is selected for screening natural gas (the main ingredient is methane), the mobile device 100 can be used as a portable gas-sensing device to sense natural gas, thereby preventing the explosion crisis caused by natural gas leakage. A material of the filter membrane 126 is a nanoporous material, for example. The nanoporous material is a polymer or anodic aluminum oxide, for example.

Based on the above embodiments, in the mobile device 100 having the gas-sensing function, since the gas sensor 106 is integrated into the mobile device 100, the purpose of the portable gas sensing can be achieved, and the use is very convenient. Additionally, since the gas-sensing material layer 120 can be activated by the visible light emitted from the backlight module 104 to sense the gas, the mobile device 100 can sense the gas at room temperature and have the characteristics of low energy consumption and being used for a long time. Furthermore, the gas sensor 106 in the mobile device 100 can be manufactured in a low cost manner, and the manufacturing process thereof is very flexible.

In summary, in the mobile device having the gas-sensing function of the above embodiments, since the gas sensor is integrated into the mobile device, and the gas-sensing material layer can be activated by the visible light emitted from the backlight module to sense the gas, the mobile device can achieve the purpose of the portable gas sensing and can sense the gas at room temperature.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A mobile device having a gas-sensing function, comprising:
    a case body having at least one through hole;
    a backlight module disposed in the case body; and
    a gas sensor disposed in the case body and comprising a gas-sensing material layer for sensing a gas, wherein the gas-sensing material layer receives a visible light emitted from the backlight module and is activated by the visible light, and an existence of the gas is determined by measuring a change of a resistance value of the activated gas-sensing material.

2. The mobile device having the gas-sensing function according to claim 1, wherein the at least one through hole comprises a through hole of a loudspeaker, a through hole of a microphone, or an air guide through hole of the mobile device.

3. The mobile device having the gas-sensing function according to claim 1, wherein the backlight module has a light guide plate, the light guide plate comprises a light emitting surface, a light incident surface, a sub-light emitting surface, and a bottom surface, the light emitting surface is disposed opposite to the bottom surface, the light incident surface is disposed opposite to the sub-light emitting surface, and the gas sensor is coupled to the sub-light emitting surface of the light guide plate or disposed at a back surface of the backlight module.

4. The mobile device having the gas-sensing function according to claim 1, wherein an energy gap of the gas-sensing material layer is 1.24 eV to 12.4 eV.

5. The mobile device having the gas-sensing function according to claim 1, wherein a material of the gas-sensing material layer comprises metal oxide or grapheme oxide.

6. The mobile device having the gas-sensing function according to claim 5, wherein the metal oxide comprises tungsten oxide or iron oxide.

7. The mobile device having the gas-sensing function according to claim 1, wherein a method of forming the gas-sensing material layer comprises a three dimensional printing method, an inkjet printing method, a gravure printing method, a screen printing method, a flexo printing method, or an offset printing method.

8. The mobile device having the gas-sensing function according to claim 1, wherein a gas sensed by the gas sensor comprises volatile organic compounds or carbon dioxide.

9. The mobile device having the gas-sensing function according to claim 1, wherein the gas sensor further comprises a first electrode and a second electrode, wherein the first electrode and the second electrode are separate from each other and connected to the gas-sensing material layer.

10. The mobile device having the gas-sensing function according to claim 1, wherein the gas sensor further comprises a filter membrane, wherein the filter membrane covers the gas-sensing material layer.

11. The mobile device having the gas-sensing function according to claim 10, wherein a material of the filter membrane comprises a nanoporous material, and the nanoporous material comprises polymers or anodic aluminum oxide.

12. The mobile device having the gas-sensing function according to claim 1, wherein the mobile device comprises a mobile phone, a tablet computer, a notebook computer, a portable game machine, or a portable music player device.

* * * * *